(12) United States Patent
Rick et al.

(10) Patent No.: US 10,408,648 B2
(45) Date of Patent: Sep. 10, 2019

(54) FLOW METER WITH ADAPTABLE BEAM CHARACTERISTICS

(71) Applicant: Hach Company, Loveland, CO (US)

(72) Inventors: David L. Rick, Longmont, CO (US);
Ernie Ray Paoli, Loveland, CO (US);
Philip N. King, Timnath, CO (US)

(73) Assignee: HACH COMPANY, Loveland, CO (US)

( * ) Notice: Subject to any disclaimer, the term of this patent is extended or adjusted under 35 U.S.C. 154(b) by 193 days.

(21) Appl. No.: 15/198,911

(22) Filed: Jun. 30, 2016

(65) Prior Publication Data

US 2018/0003535 A1   Jan. 4, 2018

(51) Int. Cl.
*G01F 1/66* (2006.01)
*G01F 1/00* (2006.01)
*G01P 5/24* (2006.01)
*G01N 29/024* (2006.01)

(52) U.S. Cl.
CPC .............. *G01F 1/66* (2013.01); *G01F 1/002* (2013.01); *G01F 1/663* (2013.01); *G01N 29/024* (2013.01); *G01P 5/241* (2013.01)

(58) Field of Classification Search
CPC ........ G01S 15/50; G01S 15/582; G01S 15/88; G01S 15/588; G01S 15/895; G01S 15/8959; G01P 5/08; G01P 5/24; G01P 5/244

See application file for complete search history.

(56) References Cited

U.S. PATENT DOCUMENTS

| 4,062,237 | A | 12/1977 | Fox |
| 5,315,880 | A | 5/1994 | Bailey |
| 5,454,372 | A | 10/1995 | Banjanin et al. |
| 5,467,650 | A | 11/1995 | Cushing |

(Continued)

FOREIGN PATENT DOCUMENTS

| CN | 101936756 A | 1/2011 |
| CN | 102680977 A | 9/2012 |

(Continued)

OTHER PUBLICATIONS

Godley, Andrew, "Flow measurement in partially filled closed conduits", Flow Measurement and Instrumentation, Dec. 2002, vol. 13, Issues 5-6, pp. 197-201, Elsevier.

(Continued)

*Primary Examiner* — Mohamed Charioui
*Assistant Examiner* — Christine Y Liao
(74) *Attorney, Agent, or Firm* — Ference & Associates LLC

(57) ABSTRACT

An embodiment provides a method for measuring a fluid parameter of fluid flowing in a channel, including: transmitting, using a transmitter of a device, directed energy carrying a signal toward a surface of a fluid in a fluid channel, so as to produce one or more reflections from the fluid surface; detecting, by at least one receiver of the device, one or more received signals associated with the one or more reflections so produced; and determining, based upon a measurement beam comprising characteristics of the transmitted and received signals, a fluid parameter to be measured using a processor of the device; wherein, a measurement beam characteristic is adjusted based on a distance from the device to the fluid surface. Other embodiments are described and claimed.

20 Claims, 11 Drawing Sheets

(56) References Cited

U.S. PATENT DOCUMENTS

| | | |
|---|---|---|
| 5,515,721 A | 5/1996 | Kim et al. |
| 5,522,393 A | 6/1996 | Phillips et al. |
| 5,531,125 A | 7/1996 | Ahn et al. |
| 5,564,424 A | 10/1996 | Yao |
| 5,623,930 A | 4/1997 | Wright et al. |
| 5,684,250 A | 11/1997 | Marsh et al. |
| 5,734,111 A | 3/1998 | Hak Soo |
| 5,780,747 A | 7/1998 | Soo |
| 5,811,688 A | 9/1998 | Marsh et al. |
| 5,821,427 A | 10/1998 | Byrd |
| 5,952,583 A | 9/1999 | Chang |
| 6,535,835 B1 | 3/2003 | Rubin et al. |
| 6,545,286 B1 | 4/2003 | Ross et al. |
| 6,647,804 B1 | 11/2003 | Deines |
| 7,539,082 B2 | 5/2009 | Vogt |
| 7,542,374 B2 | 6/2009 | Brumley et al. |
| 7,839,720 B2 | 11/2010 | Brumley et al. |
| 7,847,925 B2 | 12/2010 | Vogt |
| 8,215,183 B2 | 7/2012 | Petroff |
| 8,339,584 B2 | 12/2012 | Christian et al. |
| 8,434,371 B2 | 5/2013 | Marsh |
| 2011/0000311 A1 | 1/2011 | Petroff |
| 2013/0000416 A1 | 1/2013 | Croft et al. |
| 2013/0345994 A1 | 12/2013 | Wiklund et al. |
| 2014/0202240 A1 | 7/2014 | Skinner et al. |
| 2014/0230567 A1* | 8/2014 | Rowe .................. G01F 1/667 73/861.25 |
| 2015/0007654 A1 | 1/2015 | Fehrenbach et al. |
| 2015/0007655 A1 | 1/2015 | Skowaisa |
| 2015/0020608 A1 | 1/2015 | Chevrier et al. |
| 2016/0138950 A1 | 5/2016 | Sevar |

FOREIGN PATENT DOCUMENTS

| | | |
|---|---|---|
| CN | 202836680 U | 3/2013 |
| CN | 103792533 A | 5/2014 |
| DE | 3223393 A1 | 12/1983 |
| DE | 4016529 C1 | 11/1991 |
| DE | 4228977 A1 | 3/1994 |
| DE | 10134264 A1 | 2/2003 |
| EP | 0550735 A1 | 7/1993 |
| GB | 2376740 A | 12/2002 |
| GB | 2393783 A | 4/2004 |
| JP | 2011122831 A | 6/2011 |
| JP | 2016114358 A | 6/2016 |
| WO | WO2001051897 A1 | 7/2001 |
| WO | WO2008039948 A2 | 4/2008 |
| WO | WO2010057480 A2 | 5/2010 |

OTHER PUBLICATIONS

Larrarte, Frederique, "Velocity fields within sewers: An experimental study", Flow Measurement and Instrumentation, Oct. 2006, vol. 17, Issue 5, pp. 282-290, Elsevier.

Teague, Calvin C. et al., "Canal and river tests of a RiverSonde streamflow measurement system", IEEE 2001 International Geoscience and Remote Sensing Symposium (IGARSS '01), Jul. 9-13, 2001, Sydney, NSW, 3 pages, IEEE Digital Library.

Fulton, John et al., "Measuring real-time streamflow using emerging technologies: Radar, hydroacoustics, and the probability concept", Journal of Hydrology, Jul. 30, 2008, vol. 357, Issues 1-2, pp. 1-10, Elsevier.

Kouyi, G.L. et al., "Use of cfd technique to optimize flowmeters location in sewers", Definition of methods for optimal microlocation of sensors in sewers, Dec. 20, 2011, 66 pages, European Commission Report, Prepared 2011.031, Copy available at: http://www.prepared-fp7.eu/viewer/file.aspx?fileinfoID=203.

R. Mohn et al., "Influence of Pipe-Junctions on Downstream Measuring Sections, predicted by a numerical model," Novatech 2010, 10 pages, Copy available at: http://documents.irevues.inist.fr/bitstream/handle/2042/35751/22507-212MOH.pdf.

International Search Report and Written Opinion, dated Jan. 4, 2018, pp. 15.

* cited by examiner

FLOW METER WITH ADAPTABLE BEAM CHARACTERISTICS

BACKGROUND

The measurement of open channel flow in municipal wastewater collection systems is important to protect public health, municipal infrastructure, and the environment. Raw (untreated) drinking water, irrigation water, and plant effluent water are also transported via engineered open channels and pose similar measurement challenges. Accurate flow metering is necessary for billing, engineering studies, mitigation of unwanted inflow and infiltration, and for the control of the actual flow itself. Flow volumes must be understood and managed to minimize the impact of peak flows on wastewater treatment facilities and to reduce the possibility of untreated sewage reaching the environment.

There are a number of open channel flow meters in existence today. For example, there is a flow meter for measuring both the fluid velocity and the fluid level by non-invasive level sensors and velocity sensors that can be mounted inside a manhole above the flowing channel (typically just above the top of the pipe or culvert, a crown mount). The velocity and level signals can be combined with knowledge of the pipe geometry, and by using a surface velocity modifier, the instrument electronics converts the sensed surface velocity to approximate the cross-sectional average velocity of the stream.

By way of example, a carrier frequency signal may be directed toward the surface of a fluid flowing in an open channel. More particularly, the signal is directed along a line toward the fluid surface and at least a portion of the signal is reflected from the fluid surface, and the Doppler frequency shift between the directed and reflected signals is used as a measure of the velocity of the fluid surface. Typically, a non-invasive measure of the fluid depth is also obtained, e.g., using downward-looking ultrasonic or other measurement techniques. From the measurements of velocity and depth, the flow rate of the fluid is calculated.

BRIEF SUMMARY

One embodiment provides a method for measuring a fluid parameter of fluid flowing in a channel, comprising: transmitting, using a transmitter of a device, directed energy carrying a signal toward a surface of a fluid in a fluid channel, so as to produce one or more reflections from the fluid surface; detecting, by at least one receiver of the device, one or more received signals associated with the one or more reflections so produced; and determining, based upon a measurement beam comprising characteristics of the transmitted and received signals, a fluid parameter to be measured using a processor of the device; wherein, a measurement beam characteristic is adjusted based on a distance from the device to the fluid surface.

Another embodiment provides a device for measuring a fluid parameter of fluid flow in a channel, comprising: a transmitter; at least one receiver; a processor operatively coupled to the at least one transmitter and the at least one receiver; a memory device that stores instructions executable by the processor to: transmit, using the transmitter, directed energy carrying a signal toward a surface of a fluid in a fluid channel, so as to produce one or more reflections from the fluid surface; detect, by the at least one receiver, one or more received signals associated with the one or more reflections so produced; and determine, based upon a measurement beam comprising characteristics of the transmitted and received signals, a fluid parameter to be measured; wherein a measurement beam characteristic is adjusted based on a distance from the device to the fluid surface.

A further embodiment provides a product for measuring velocity of fluid flow in a channel, comprising: a storage device having code stored therewith, the code being executable by a processor and comprising: code that transmits, using a transmitter of a device, directed energy carrying a signal toward a surface of a fluid in a fluid channel, so as to produce one or more reflections from the fluid surface; code that detects, by at least one receiver of the device, one or more received signals associated with the one or more reflections so produced; and code that determines, based upon a measurement beam comprising characteristics of the transmitted and received signals, a fluid parameter to be measured using a processor of the device; wherein, a measurement beam characteristic is adjusted based on a distance from the device to the fluid surface.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
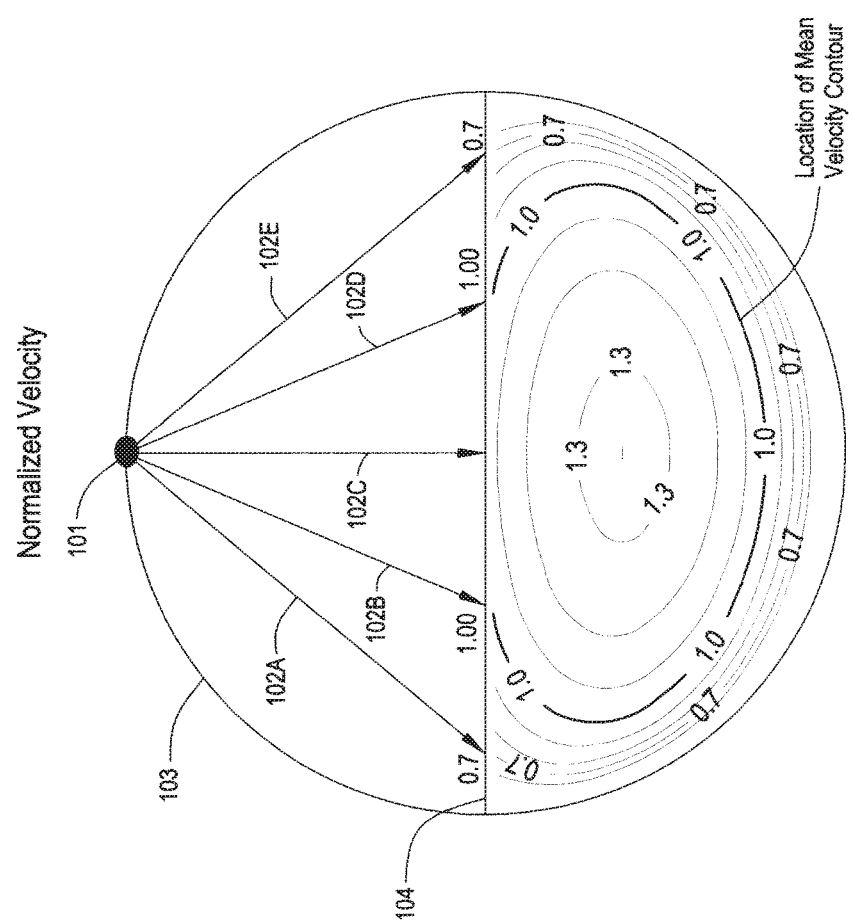
FIG. 1 illustrates a cross sectional view of a fluid flow meter measuring multiple surface velocities of a fluid in a pipe.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

A drawback in non-contact or surface measurement techniques is that the measurement of surface velocity does not necessarily represent the mean velocity of the fluid being measured. This is true because fluid velocities vary across the width of the channel, and also from surface to channel bottom the velocity distribution is variable, depending upon channel slope, friction, fluid characteristics, and the flow conditions upstream and downstream of the measurement location.

Measurement of volumetric flow (Q) in an open channel context where a pipe or other fluid conduit has a defined cross-section are based on the area-velocity concept:

$$Q=VA,$$

where A is the area of a filled channel cross-section, and V is the average fluid velocity through that area, also known as the cross-sectional average velocity.

In harsh environments such as underground fluid conduits, non-contact measurement technologies are particularly desirable due to lower maintenance costs. HACH Company's existing FLO-DAR product provides non-contact measurement of average velocity (V) and area (A). The FLO-DAR product utilizes a radar-based measurement of surface velocity and an ultrasonic measurement of fluid level, although other measurement techniques may be employed. FLO-DAR is a registered trademark of Hach Company in the United States and other countries.

The surface velocity measurable using for example a radar beam or an ultrasonic beam is generally not the same as the true cross-sectional average velocity, V, i.e., that which is needed to accurately compute volumetric flow. The measured surface velocity must be modified according to some algorithm in order to obtain an estimate of cross-sectional average velocity. The need to estimate a cross-sectional average velocity from velocity observations within a centrally-disposed surface patch, where a radar beam or other measurement beam intersects the water surface, is a source of potential error.

Typically, installers of existing non-contact sensors use a manual velocity profiling method, such as a pole-mounted point-velocity sensor, to "profile" the channel and develop a site-specific correction which is subsequently applied to readings from a non-contact velocity sensor measuring surface velocity at a single point or localized patch. It is questionable whether a simple correction factor derived at installation time is adequate for use over time and under a variety of flow conditions encompassing varying fluid heights and changing channel conditions.

It follows that a sensor capable of measuring surface velocity at multiple locations across the width of a channel has the potential to allow better estimation of cross-sectional average velocity. An embodiment therefore provides for and uses a multiplicity of measured surface velocities to obtain an estimate of the cross-sectional average velocity.

An embodiment also changes, adjusts, or steers the beam(s) in order to measure different positions or widths based on a level of the fluid within the channel.

The illustrated example embodiments will be best understood by reference to the figures. The following description is intended only by way of example, and simply illustrates certain example embodiments.

In FIG. 1 there is illustrated a fluid flow meter 101 positioned to measure flow of a fluid 104 in a fluid channel 103. This cross-sectional view illustrates that the fluid 104 flows through the fluid channel 103 with varying velocities, as indicated for example by the representative velocity contour lines. The mean velocity contour line is indicated. This location of the mean velocity may vary, and is often influenced by the fluid conduit or channel, e.g., the fluid 104 flows at higher speeds at the internal center of the fluid 104, with the edges of the fluid 104 proximate to the channel 103 (sides and bottom) flowing more slowly.

As may be appreciated from reviewing FIG. 1, and the velocity contours of the fluid 104, taking a singular measurement (e.g., using only beam 102c) may not yield a particularly accurate or representative velocity estimate, e.g., useful in terms of measuring fluid flow. Thus, an embodiment provides a fluid flow meter 101 that measures flow of the fluid 104 within the channel 103 by measuring a plurality of surface points. By way of example, as illustrated in FIG. 1, an embodiment utilizes a plurality of beams 102a, 102b, 102c, 102d and 102e in order to obtain velocity measurements at different points of the fluid 104. As will be apparent from the description herein, more or fewer beams than those illustrated in FIG. 1 may be utilized. The number of beams may vary, for example, based on the width of the fluid channel 103, the mounting height of the flow meter 101, the distance between the flow meter (or component thereof, e.g., transducer and/or receiver) and the fluid surface (e.g., for a mobile flow meter that varies in height above the fluid channel), the type of beam(s) utilized, and/or the fluid level within the fluid channel 103.

Figure 2:
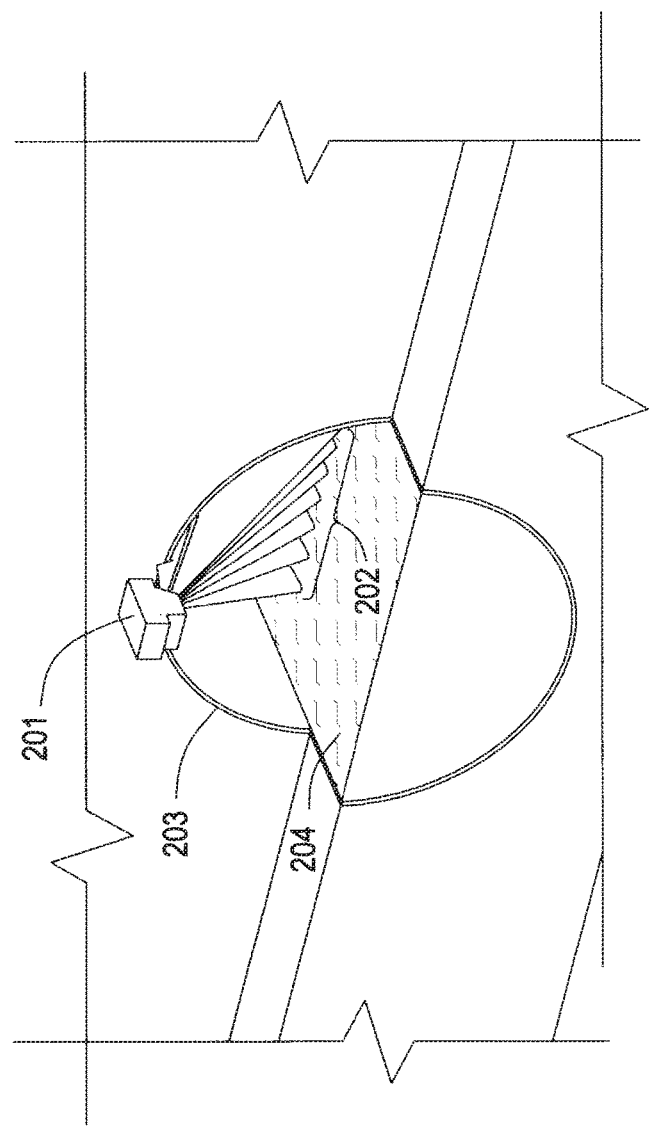
FIG. 2 illustrates a cross perspective view of a fluid flow meter measuring multiple surface velocities of a fluid in a pipe.

Illustrated in FIG. 2 is an example implementation of a fluid flow meter 201 according to an embodiment. The fluid flow meter 201 provides a fluid flow measurement based on a plurality of beams 202, where the beam characteristics permit measuring velocity at a multiplicity of locations on the fluid surface 204; here, the beams are illustrated as substantially spanning the width of a fluid channel 203.

The flow meter 201 may include a radar-based sensor or transducer capable of transmitting and receiving the plurality of beams 202 used for measuring surface velocity of the fluid 204 (e.g., water) at a multiplicity of locations substantially spanning the width of an open channel 203. The radar-based sensor of the fluid flow meter 201 may achieve measurements of velocity at multiple points by steering a single radar beam to multiple points on the fluid 204 surface, by switching among several beams having fixed orientations in terms of the fluid 204 surface, or a suitable combination of the foregoing. The flow meter 201 may employ a single transmit/receive antenna (or array) or may use one or more dedicated transmit antennas (or arrays) and one or more dedicated receiver antennas (or arrays).

In a flow meter 201 employing distinct transmit and receive antennas, the steering or switching may be applicable only to receive antennas, only to transmit antennas, or to both. When only one of receive antenna(s) or transmit antenna(s) is steered or switched, the other may employ a wide beam shape capable of substantially spanning the channel 203 without re-direction. While transmit and receive beams may have distinct radiation/reception patterns, it is sometimes useful to consider an effective beam pattern for a round-trip path of energy propagating from a transmitting antenna to a target and returning to a receiving antenna. This effective beam pattern for a round-trip path of energy is referred to as a "measurement beam" governed by the combined characteristics of the transmit and receive antennas. Persons skilled in the art will recognize that the measurement beam has a pattern comprising the product of the associated transmit and receive patterns, and the measurement beam pattern may be changed by modifying either or both.

The number of resulting measurement beams may be greater than or equal to the number of transmit or receive beams. For example, combining 2 transmit beams, angularly selective in elevation, with 3 receive beams, angularly selective in azimuth, may yield 6 distinguishable measurement beams.

Figure 3:
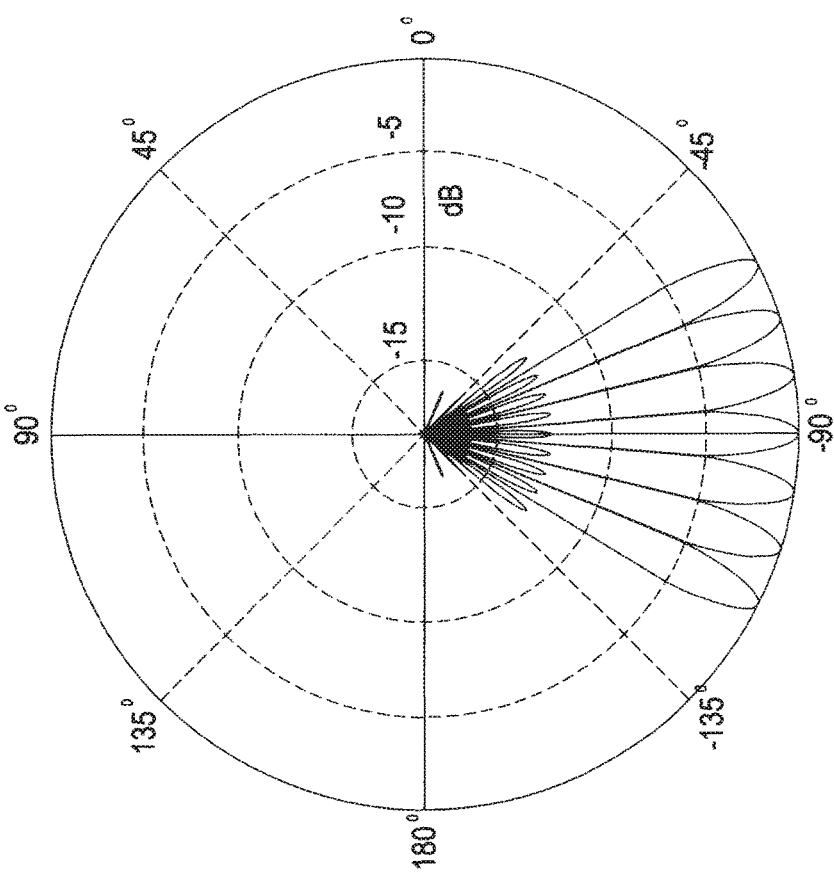
FIG. 3 illustrates an example beam array provided by an antenna array.

A flow meter, e.g., 101, 201, may utilize a plurality of fixed antenna elements, for example arranged as a linear or planar array. Such arrangements may be used for a transmitting antenna, a receiving antenna, or both. By way of non-limiting example, and referring to FIG. 3, the transmit antennas may be provided in an array, e.g., a fixed linear array, such that the resulting measurement beams cover (are reflected from) the surface of the fluid 104 in distinct areas. FIG. 3 illustrates an example of the azimuthal pattern (power vs. angle) for 7 distinct measurement beams produced using an antenna array having 13 elements spaced at 7.5 mm.

One method of controlling beam direction involves applying progressive phase or time delays to the elements of a phased-array antenna. Those skilled in relevant art will recognize that there exist a variety of ways of steering or switching among distinctly-steered measurement beams and the scope of the described embodiments defined by claims should not be limited by which particular method is used, unless explicitly stated in one or more of the claims.

In the example of FIG. 3, the elements of the array may be controlled to produce the 7 measurement beams indicated. This provides, for a receiving antenna located in (or in operative connection with) a fluid flow meter, 101, 201, a plurality of measurements of the surface velocity of the fluid, e.g., as illustrated in FIG. 2. Note that more or fewer transmission beams may be utilized.

A non-contact fluid velocity sensor may be disposed in a fluid flow meter 101, 201 for use in open channels, e.g., 103 of FIG. 1 or 203 of FIG. 2. The non-contact fluid velocity sensor is capable of measuring surface velocity at a multiplicity of locations substantially spanning the channel's width, as for example illustrated in FIG. 2. The non-contact fluid velocity sensor may employ one or more electromagnetic beams, e.g., the sensor may employ a radar-based beam system for Doppler surface velocity determination. It is noted that the non-contact fluid velocity sensor may employ other techniques, e.g., one or more ultrasonic beams.

A radar system employed by a flow meter such as meter 101 or 201 may include measurement beam(s) utilizing vertical electromagnetic polarization and designed for a beam angle of between about 25 and about 45 degrees above the fluid surface 104, where about 35 degrees is the most-preferred angle.

Meter electronics, further described herein, may use at least two surface velocities measurements from the fluid to estimate a parameter of an open channel flow velocity model. By way of example, the meter electronics may contain a memory that stores an application containing therein an open channel flow velocity model, where the application permits fluid flow to be estimated given input surface velocity measurements from a plurality of surface locations. In an embodiment, any one of, or several of, the following analysis techniques may be used to apply these measured surface velocities to useful purposes.

By way of example, the individual surface velocity measurements may be used directly in a multi-dimensional equation or table to determine the cross-sectional average velocity. The multi-dimensional equation or table may be derived according to theoretical precepts, empirical studies, or some combination thereof. In an embodiment, such data may be contained on board in a memory of a flow meter such as flow meter 101, or may be accessed by way of wired or wireless communication between the flow meter and another device.

In addition, or in the alternative, measured surface velocities may be used to fit a parametric velocity model describing velocities across the entire channel cross-section. The fitted model may then be used to compute the required average velocity.

In addition, or in the alternative, measured surface velocities may be used to fit a low-order parametric model of the surface velocity distribution, for instance a quasi-parabolic model parameterized by central velocity, width, and skew. The resulting simplified surface distribution may then be used to estimate cross-sectional average velocity according to some theoretical model or empirically-derived calibration rule.

In addition, or in the alternative, the measured surface velocities may be used to infer relevant physical characteristics of the channel, for instance the surface roughness of one or more channel boundaries or one or more boundary shear values.

In addition, or in the alternative, the surface velocity measurements may be compared to a library of computer simulation results to determine which simulation best matches the observed surface velocity data and the cross-sectional average velocity may be inferred by re-scaling the average velocity from the chosen simulation.

In applying any of these methods, enumerated by way of example, a time-averaged or smoothed version of the surface velocity measurements may be utilized.

In an embodiment, transmit or receive beams used by a flow meter, e.g., flow meter 101 of FIG. 1, may be adapted or changed based on the fluid 104 level within a channel 103. By way of example, for non-rectangular channels, such as the fluid channel 103 illustrated in FIG. 1, the number of locations measured may vary with the channel's fluid fill level. By way of specific example, in a channel such as channel 103 having a substantially circular cross-section, the number of fluid surface measurement locations is to be maximized at about 50 percent fill level, as this is the fill point at which a maximal fluid surface width is achieved within the channel 103. At very low or very high fill levels of a circular cross-section channel 103, it may be sufficient to employ only a single centrally disposed beam because the width of that beam already spans the fluid 104 surface.

Turning to FIG. 4 through FIG. 9, an example embodiment that modulates, changes or adjusts the beam(s) based on the fluid level is described.

Figure 4:
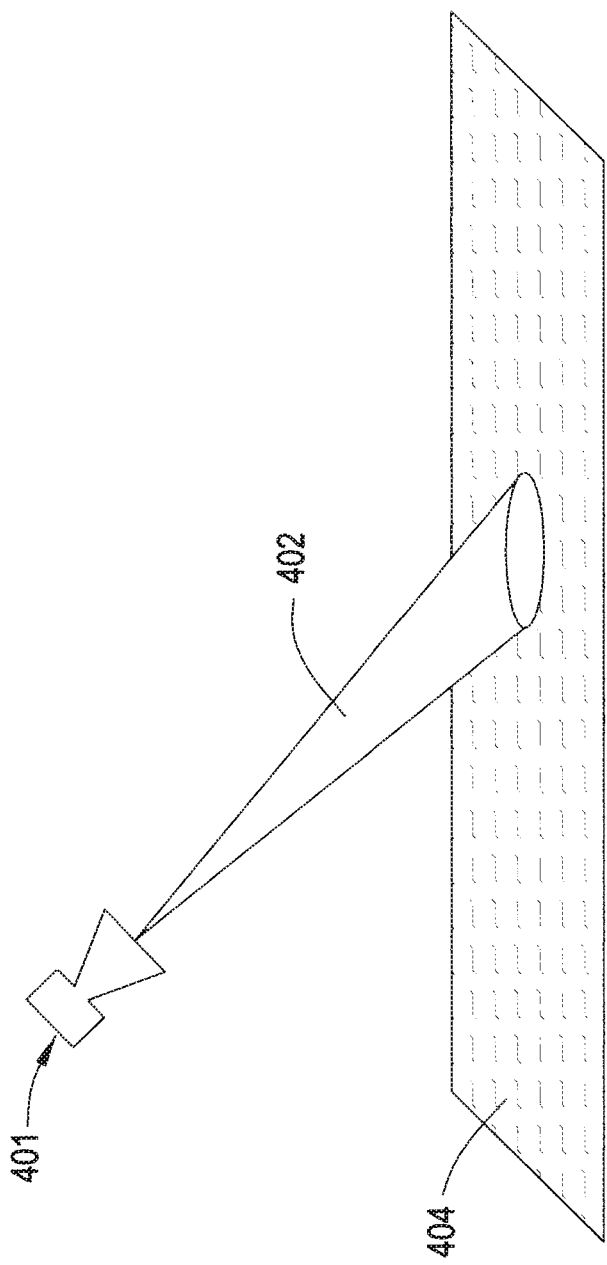
FIG. 4 illustrates a beam surface characteristic.

As illustrated in FIG. 4, most flow meters, e.g., 401, include a transducer, whether electromagnetic or acoustic, to produce a beam 402 whose shape can be approximated as circular or flattened cone having its apex at the transducer.

This cone, projected on the fluid surface 404, produces a measurement patch whose shape may be circular, ovaloid, or teardrop-shaped.

Figure 5:
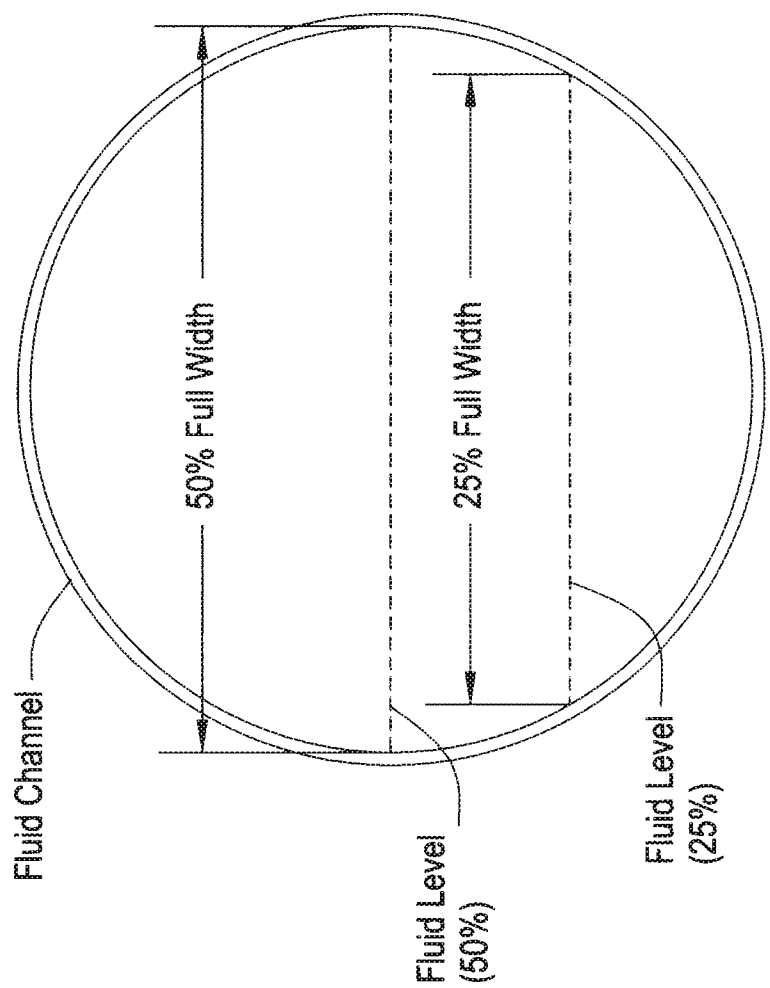
FIG. 5 illustrates differing fluid levels and fluid surface dimensions in a pipe.

If the distance between the flow meter 401 transducer and the fluid surface 404 is variable, for example as often occurs in an underground wastewater fluid channel, then the measurement patch size will change as well. Frequently in underground wastewater fluid channel monitoring, and occasionally in surface water monitoring, cases are encountered in which large variations of fluid depth are possible. At some time, the fluid surface 404 is quite close to the flow meter 401, while in other cases it is much farther away. Furthermore, in open-channel flow measurement, the channel cross-section may be non-rectangular (i.e., conduits of circular cross-section are common), and in such channels the width of the fluid surface 404 will vary with fluid levels, as illustrated in FIG. 5, where fluid levels of 25% and 50% are illustrated.

These facts and situations create a potential need to modify the beam pattern in order to maintain an acceptably-sized measurement patch as the fluid level changes. The particular fluid level at which such modification should be made may depend also on site and installation specifics, such as channel shape and instrument mounting location.

Figure 6:
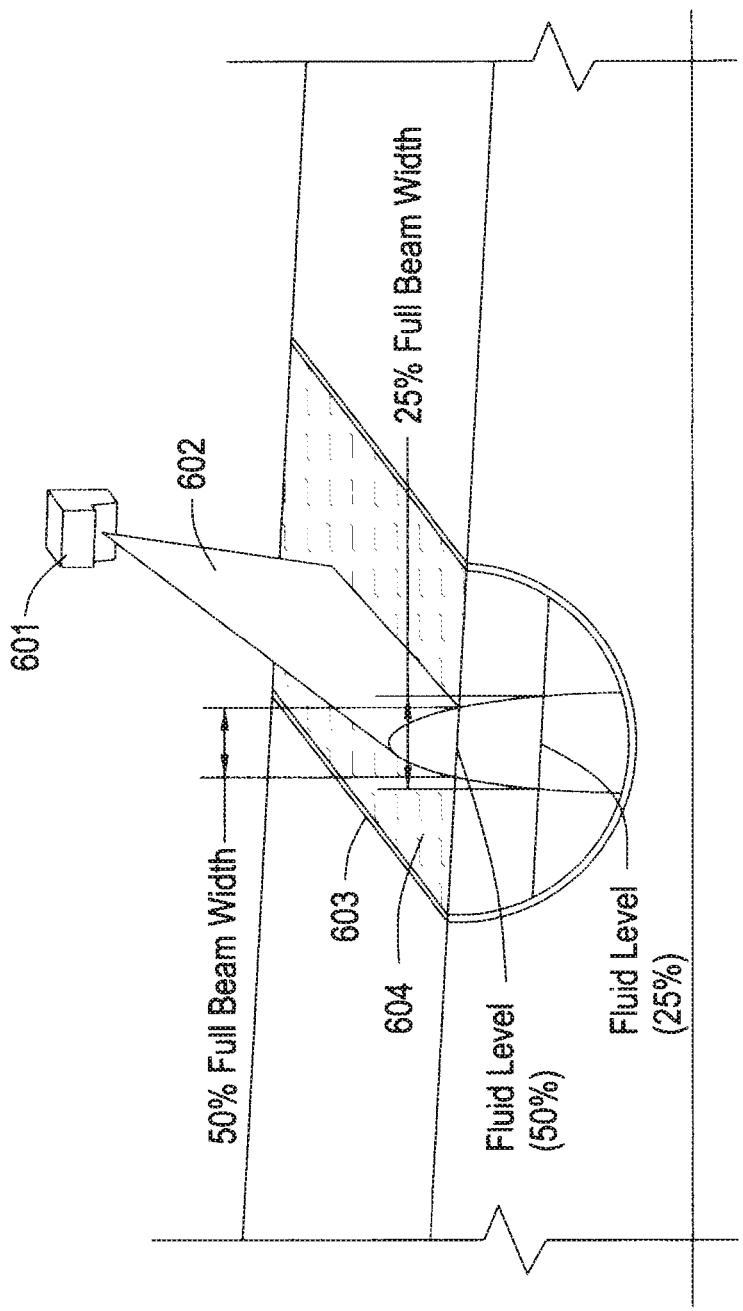
FIG. 6 illustrates an example of beam width differences based on fluid level.

FIG. 6 illustrates the variation of a projected beam 602 in terms of width as the distance between the transducer of the flow meter 601 and the fluid surface 604 changes within the fluid channel 603. It will be noted that, in non-rectangular channels, a change in fluid level will also cause the surface width of the fluid 604 to change. These effects are independent.

Figure 7:
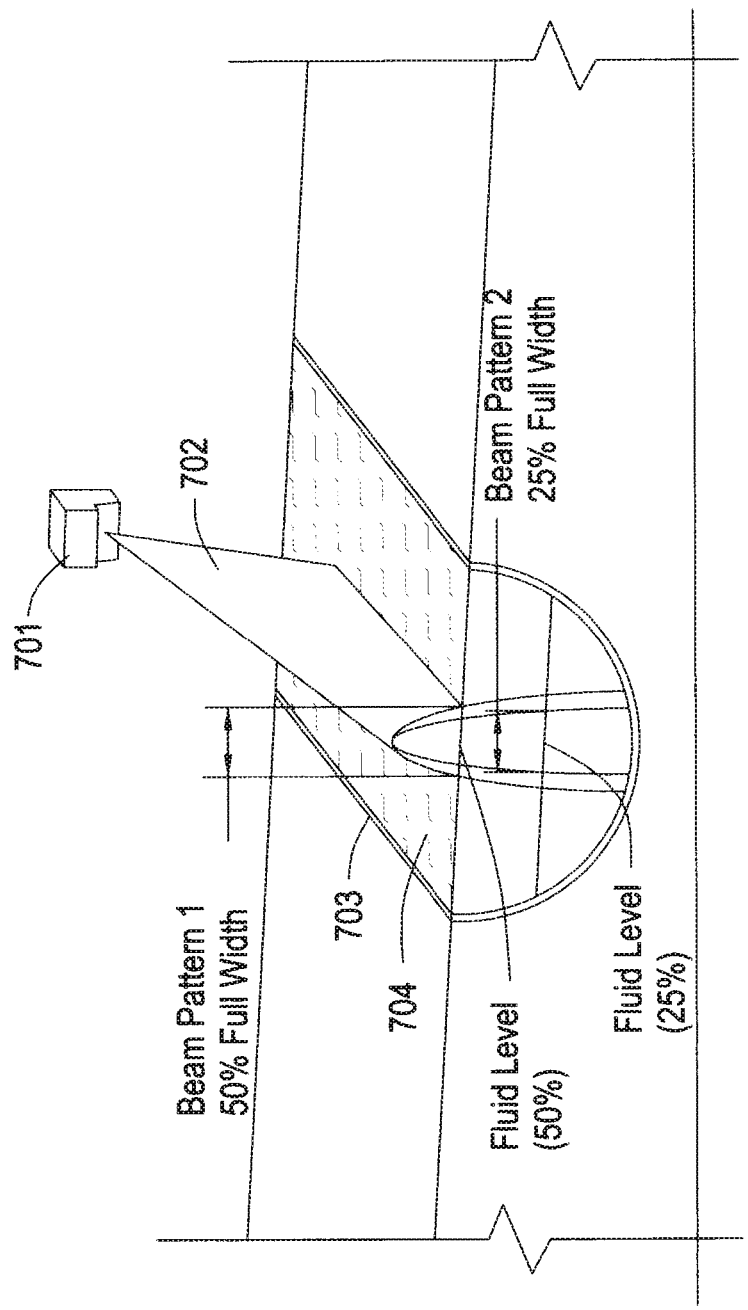
FIG. 7 illustrates an example of beam width adaptation based on fluid level.

Accordingly, as illustrated in FIG. 7, an embodiment intentionally adapts the width of the beam 702 according to fluid height in order to hold the projected beam width at the fluid surface, e.g., 704 at 50% fluid level, constant or nearly so. Thus, beam 702 is adjusted to be wider at 50% fill level, as the fluid level 704 is closer to flow meter 701, as compared to the beam width used at 25% fill level, as illustrated in FIG. 7. Thus, an embodiment intentionally adapts the beam 702 such that approximately the same beam width contacts the fluid surface, irrespective of the fluid level.

Alternatively (not shown in FIG. 7), the beam 702 may be adapted with fluid height so as to hold the ratio of its projected width to the fluid surface width constant. This may require an adaptation rule specific to the channel shape, as the fluid surface width modulates differently based on the fill level and fluid channel 703 shape.

Beam directivity is primarily governed by the square of the transducer size relative to the wavelength of the transmitted or received energy. This statement is true when the beam pattern is observed in the far field region beyond some minimum distance from the transducer. In simple cases, the far field boundary distance is given by $2D^2/\lambda$, where D is the span of the transducer face and $\lambda$ is the wavelength of the transmitted or received energy. A transducer employed at ranges less than the far field boundary distance may exhibit degradation of its intended beam pattern, for instance higher side lobe levels. If a transducer is to be used at short ranges, it may be desirable to employ a less-directional (smaller) design, in order to shorten the far field distance. However, if the transducer must also be used at longer ranges, compromising its directivity may be undesirable because it will result in an excessively large measurement patch. Some installation sites exhibit wide variation in the fluid levels and thus the range between transducer and fluid surface. Thus, there is a potential need to modify the transducer's effective size as the fluid level changes. The fluid level at which this problem manifests will depend on site and installation specifics such as channel shape and instrument mounting location.

A characteristic of fluid flow measurement instruments (apart from the type of beam energy employed) is that some use monostatic transducers, while others use bistatic transducers. Monostatic transducers both transmit and receive using the same transducer, while a bistatic transducer instrument uses distinct transducers for transmit and receive. Some instruments are capable of operating in continuous-wave modes, characterized by uninterrupted operation of the transmit transducer over the complete measurement period. Other instruments are not capable of continuous-wave modes because the transmission must be stopped, and the transducer repurposed for reception, before the return energy reflected from the water surface arrives. Thus, some instruments may suffer from a time lag defined as the minimum time interval required for repurposing the transducer. In systems intended for ranging, such as a down-looking ultrasonic level sensor, this manifests as a minimum target range at which the sensor can function. While some instruments have no lag time, they potentially suffer from parallax errors caused by transmit and receive transducers being aimed at different locations on the fluid surface.

If the fluid surface is fixed at a known distance, no difficulty arises in aiming both transducers at the same point. But some installation sites will exhibit large variability in the fluid-to-transducer distance. For example, in a fluid channel the distance may vary greatly based on changing fill levels. In these situations, and particularly with narrow beam widths, it may happen that no single orientation of transmit and receive transducers will work at all fluid levels. This creates a need reorient the beam axis of one transducer with respect to the other as the fluid level changes. The fluid level at which a beam reorientation is needed will depend on site and installation specifics such as channel shape and instrument mounting location.

Figure 8:
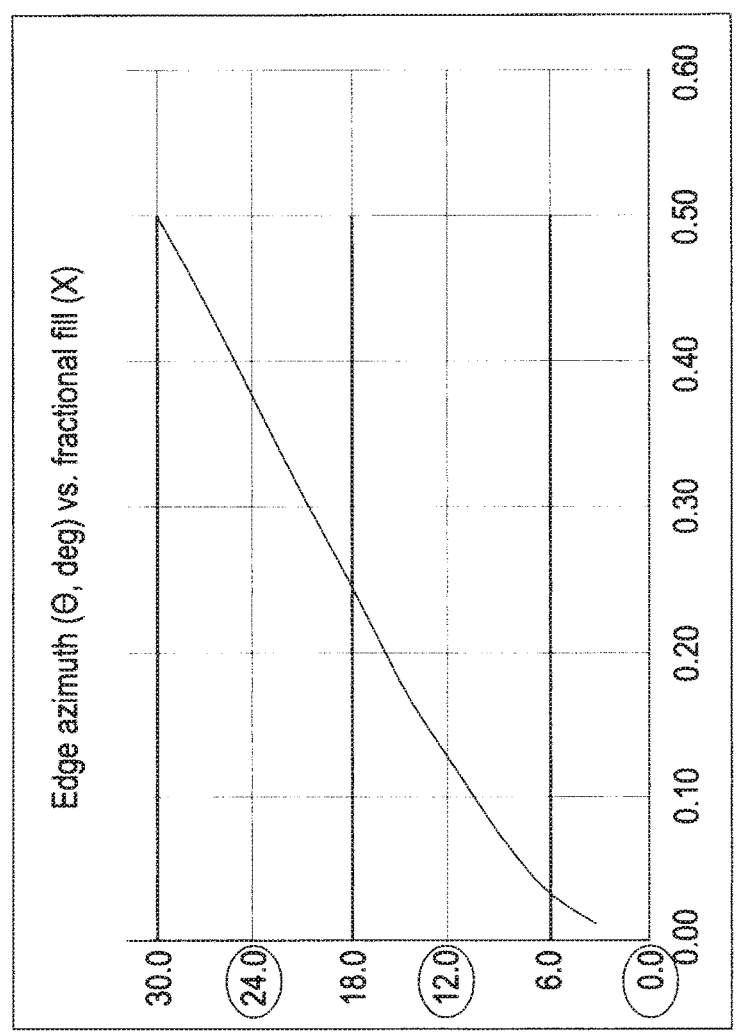
FIG. 8 illustrates example spacing of beams based on fluid level.

As the width of the fluid surface may vary with fill level, there is a need to adapt the beam orientation or active beam count as the fluid level changes. This may be done by changing the orientation of a single beam or by switching between several beams having different orientations. FIG. 8 illustrates that the required number of beams and/or their orientations may vary depending on the fluid level or generally depending on the separation between the fluid surface and the sensor(s).

In the illustrated example of FIG. 8, five beam orientations are needed when the fluid channel (e.g., pipe) is 50% full, while fewer are needed when the fill level is below 25% (or above 75%). FIG. 8 illustrates the fluid surface width of circular channel as fill varies from 0 to 50%. From 50% to 100%, the curve is mirrored. The horizontal line annotation shows that five beams having beam widths of 12° (±6°) and oriented at 0°, ±12°, and ±24° can span the entire channel surface at 50% fill. Below 25% fill, fewer beam orientations are needed.

Figure 9:
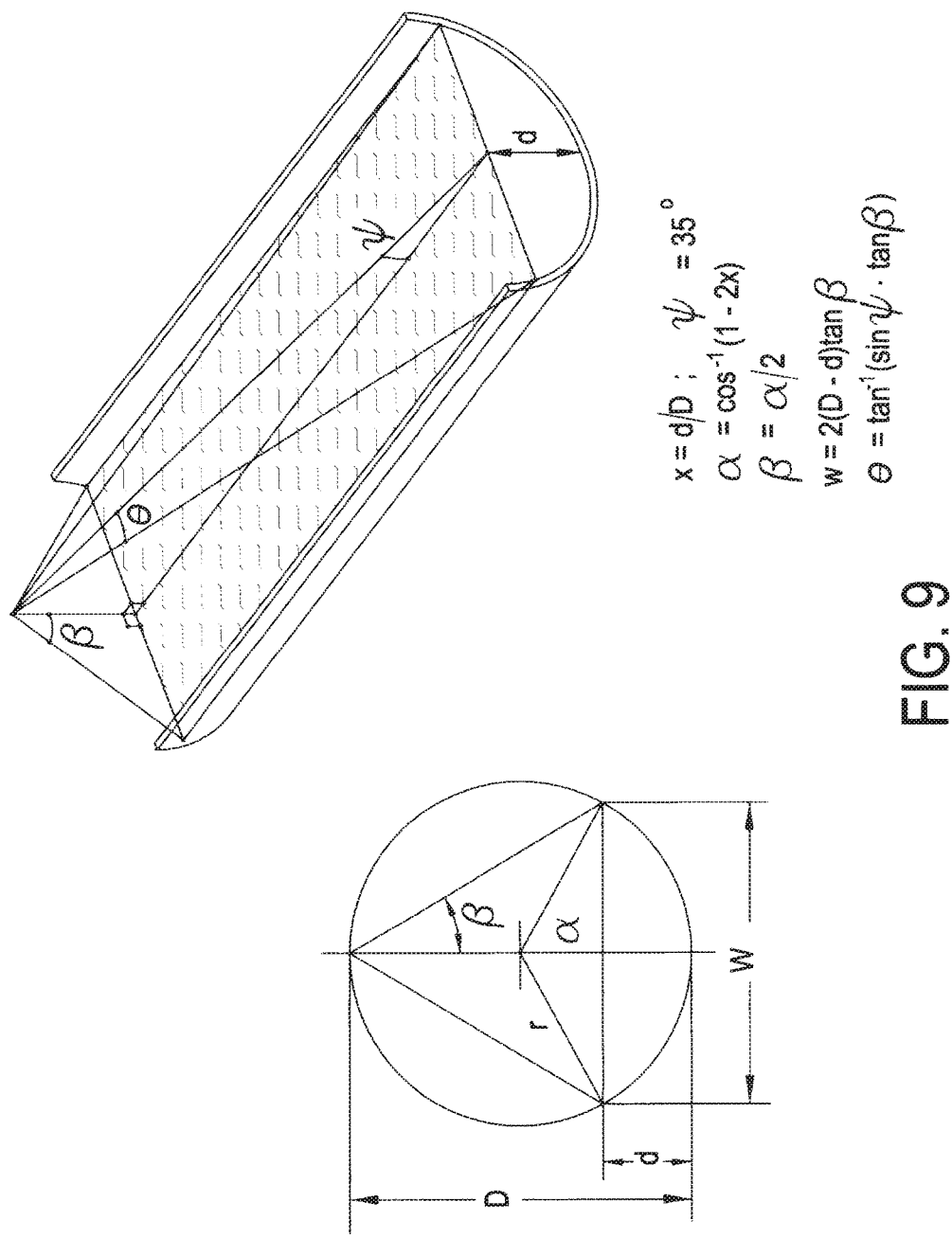
FIG. 9 illustrates example pipe geometry used to determine beam spacing.

FIG. 9 shows the geometry and equations from which the curve in FIG. 8 was calculated for a sensor mounted at the crown of a circular pipe. The equations shown in FIG. 9 may be used to derive the angle (θ) for the beam (or beams, if more than one is utilized). Using these angles, adequate fluid surface coverage may be achieved.

Thus, an embodiment provides a non-contact sensor that measures the fluid surface level and the fluid surface velocity at multiple points. The surface points chosen, or the beam width if a single beam is utilized, are varied based on the changing fluid surface width, which is correlated to the fill level in many channel types. The beam(s) used may be transmitted or received using monostatic and/or bistatic type transducers, whose beam characteristics are modified in accordance with fluid level. The characteristics to be modified may be the beam pattern or size, the beam orientation or aim, the number of active beams, or a suitable combination of the foregoing. These modifications may be achieved in one or more of the following ways, i.e., by changing the active area of the transducer so as to widen or narrow the beam width, by enabling, disabling, or changing the relative weighting of selected elements in an array-type transducer, by changing the relative phases or feed delays of various elements in an array-type transducer, by changing beam frequency or wavelength, by adjusting lenses or mirrors, and/or by switching among two or more transducers having different characteristics. Also, the characteristics of an effective measurement beam may be modified by changing the constituent transmit beam, receive beam, or both.

An embodiment therefore determines (by any means) the fluid height, e.g., a value representative of the separation between the fluid surface and the measurement instrument (or relevant component thereof). An embodiment then calculates the cross-sectional flow area and width of water surface. The measurement beam characteristics may then be adapted to the water surface width, as required, e.g., based on a different fluid level and/or a different position of the instrument, for example when the instrument is repositioned or is a mobile instrument. The instrument transmits and receives measurement beams, thereby obtaining several patch velocities, which an embodiment uses to calculate an estimated mean velocity (based on patch velocities, water height, and channel cross-section). This permits an embodiment to compute volumetric flow as mean velocity times cross sectional area. These steps may be repeated, e.g., at some later time.

Figure 10:
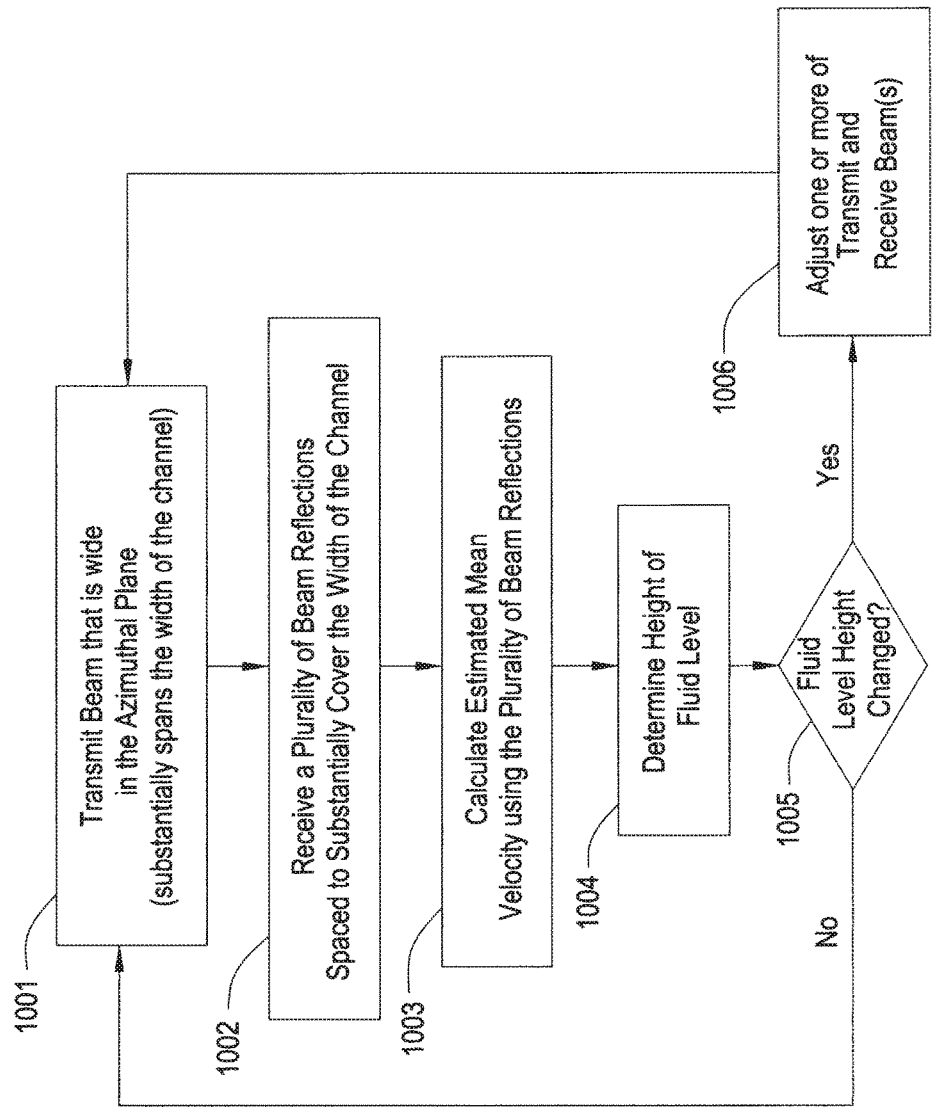
FIG. 10 outlines an example method of flow metering.

Turning to FIG. 10, an embodiment employs a set of measurement beams substantially spanning the width of the fluid channel at 1001. For example, a flow meter mounted at the top or crown of a pipe or mounted on a bridge may transmit an azimutally wide, elevationally narrow beam at an acute angle towards the fluid surface, e.g., wastewater, river water, etc. With the transmit beam spanning substantially the entire water surface, a plurality of receive beams, elevationally wide and azimuthally narrow, may be employed to measure velocities within a corresponding plurality of localized surface patches substantially spanning the width of the channel. These patches result from the fact that the effective measurement beams, being the product of transmit and receive beams, are narrow in both elevation and azimuth.

For example, in an embodiment a plurality of (e.g., five) beam reflections that are spaced, e.g., at regular angles from a center of the channel, may be received by a corresponding plurality of measurement beams. The spacing of the angles may be such that substantially the entire width of the water surface is measured, e.g., at regular increments (such as every 12 degrees (referring to FIG. 8 for example)). This spacing provides an adequate sampling in most instances to calculate a more accurate mean surface velocity for the fluid flowing through the channel as compared to a single, centrally located measurement.

An embodiment can thus use the plurality of fluid surface velocity measurements to calculate an estimated mean surface velocity at 1003. Such mean surface velocity may be converted into other useful measurements, e.g., mean fluid flow velocity and thence volumetric flow rate.

As described herein, an embodiment can adapt the transmit beam(s) and/or received beam(s) based on the fluid level. Thus, an embodiment may determine a height of the fluid level in the channel at 1004. A variety of techniques may be utilized to determine the current height of the fluid level at 1004. For example, the fluid level may be known from an initial measurement provided to the fluid flow meter and later updated (periodically, intermittently, etc.) based on a level values sensed using, e.g., a down-looking ultrasonic or microwave level measurement device If the fluid level height has changed, e.g., by at least a predetermined amount, an embodiment may adjust one or more of the transmit and receive beam(s) at 1006, i.e., prior to obtaining updated fluid surface velocity measurements. Thus, an embodiment may adjust the width of the surface being covered by a beam or beams such that an appropriate coverage is achieved for a given fluid level.

An embodiment may be implemented on a wide variety of devices. Examples of suitable devices may include a flow meter that includes an antenna array operated according to program instructions for providing a plurality of fluid surface velocity measurement points and/or a beam or beams that vary in terms of the width of the fluid surface measured, e.g., based on fill level. In an embodiment, a flow meter may include a computing device having a processor and a memory, where the processor executes instructions of a fluid surface velocity measurement program. As described herein, the memory may contain a table, model, or a combination thereof in order to use the measured surface velocity or velocities to compute an estimated fluid flow volume or rate.

Figure 11:
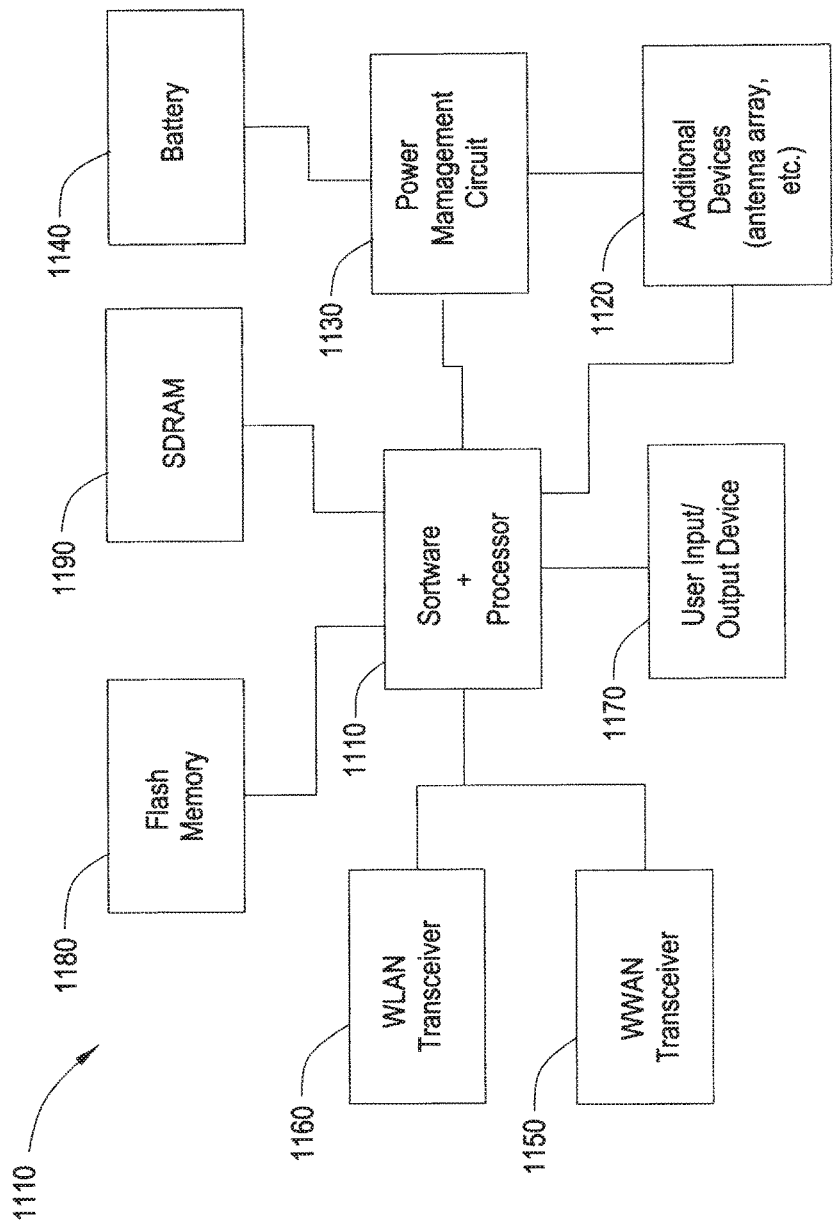
FIG. 11 illustrates an example of computer circuitry.

While various other circuits, circuitry or components may be utilized in such devices, with regard to an instrument for measuring a fluid parameter according to any one of the various embodiments described herein, an example is illustrated in FIG. 11. In some systems, one or more processor(s) 1110 are operatively coupled to certain peripherals, e.g., including signal conditioning and conversion unit 1111, memory 1112, 1113, communications interface 1114, user interface 1115, power regulation and management unit 1116, and radar subsystem 1117.

The power regulation and management unit 1116 may be powered by a rechargeable battery 1118, which may be recharged by a connection to a power source (not shown).

Additionally, peripheral devices 1119 may be included, e.g., an antenna array, as further described herein. A system often includes a user interface 1115 for data input and display/rendering. A system also typically includes various memory devices, 1112, 1113, e.g., for storing measurements reported by the antenna array 1119, for storing models or tables, etc., as further described herein.

It can be appreciated from the foregoing that electronic components of one or more systems or devices may include, but are not limited to, at least one processing unit, a memory, and a communication bus or communication means that couples various components including the memory to the processing unit(s). A system or device may include or have access to a variety of device readable media. System memory may include device readable storage media in the form of volatile and/or nonvolatile memory such as read only memory (ROM) and/or random access memory (RAM). By way of example, and not limitation, system memory may also include an operating system, application programs, other program modules, and program data.

Embodiments may be implemented as a system, method or program product. Accordingly, an embodiment may take the form of an entirely hardware embodiment, or an embodiment including software (including firmware, resident software, micro-code, etc.) that may all generally be referred to herein as a "circuit," "module" or "system." Furthermore, embodiments may take the form of a program product embodied in at least one device readable medium having device readable program code embodied thereon.

A combination of device readable storage medium(s) may be utilized. In the context of this document, a device readable storage medium ("storage medium") may be any tangible, non-signal medium that can contain or store a program comprised of program code configured for use by or in connection with an instruction execution system, apparatus, or device. For the purpose of this disclosure, a storage medium or device is to be construed as non-transitory, i.e., not inclusive of signals or propagating media.

This disclosure has been presented for purposes of illustration and description but is not intended to be exhaustive or limiting. Many modifications and variations will be apparent to those of ordinary skill in the art. The embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for measuring a fluid parameter of fluid flowing in a channel, comprising:
    transmitting, using a transmitter of a device, directed energy carrying a signal toward a surface of a fluid in a fluid channel, so as to produce one or more reflections from the fluid surface that substantially span the width of the fluid channel;
    detecting, by at least one receiver of the device, one or more received signals associated with the one or more reflections so produced; and
    determining, based upon a measurement beam comprising characteristics of the transmitted and received signals, a fluid parameter to be measured using a processor of the device, wherein the determining comprises identifying, for each of the one or more received signals, a fluid parameter corresponding to the location of the corresponding received signal and determining a mean fluid parameter from the fluid parameters for each of the one or more received signals;
    wherein, at least one measurement beam characteristic is adjusted based on a distance from the device to the fluid surface, wherein one of the at least one Measurement characteristic that is adjusted comprises a width of the measurement beam and wherein adjustment of the width of the measurement beam comprises maintaining a width of the measurement beam contacting the surface of the fluid by widening the measurement beam as the distance from the device to the fluid surface is lessened.

2. The method of claim 1, wherein:
    said measurement beam comprises a plurality of beams; and
    said measurement beam characteristic adjusted comprises a number of measurement beams.

3. The method of claim 2, wherein the number of measurement beams is increased based on the fluid level changing.

4. The method of claim 2, wherein the number of measurement beams is decreased based on the fluid level changing.

5. The method of claim 1, wherein said measurement beam comprises a plurality of measurement beams formed sequentially.

6. The method of claim 1, wherein said measurement beam comprises a plurality of measurement beams formed simultaneously.

7. The method of claim 1, wherein:
    said measurement beam characteristic adjusted comprises an angle at which said measurement beam is aimed.

8. The method of claim 1, wherein the directed energy is selected from the group consisting of a radar beam and an ultrasonic beam.

9. The method of claim 1, wherein the measurement beam is formed using at least one phased array.

10. The method of claim 1, wherein a plurality of measurement beams produce a plurality of received signals.

11. A device for measuring a fluid parameter of fluid flow in a channel, comprising:
    a transmitter;
    at least one receiver;
    a processor operatively coupled to the at least one transmitter and the at least one receiver;
    a memory device that stores instructions executable by the processor to:
    transmit, using the transmitter, directed energy carrying a signal toward a surface of a fluid in a fluid channel, so as to produce one or more reflections from the fluid surface that substantially span the width of the fluid channel;
    detect, by the at least one receiver, one or more received signals associated with the one or more reflections so produced; and
    determine, based upon a measurement beam comprising characteristics of the transmitted and received signals, a fluid parameter to be measured, wherein the determining comprises identifying, for each of the one or more received signals, a fluid parameter corresponding to the location of the corresponding received signal and determining a mean fluid parameter from the fluid parameters for each of the one or more received signals;
    wherein at least one measurement beam characteristic is adjusted based on a distance from the device to the fluid surface, wherein one of the at least one measurement characteristic that is adjusted comprises a width of the measurement beam and wherein adjustment of the width of the measurement beam comprises maintaining a width of the measurement beam contacting the surface of the fluid by widening the measurement beam as the distance from the device to the fluid surface is lessened.

12. The device of claim 11, wherein:
    said measurement beam comprises a plurality of beams; and
    said measurement beam characteristic adjusted comprises a number of measurement beams.

13. The device of claim 12, wherein the number of measurement beams is increased based on the fluid level changing.

14. The device of claim 12, wherein the number of measurement beams is decreased based on the fluid level changing.

15. The device of claim 11, wherein said measurement beam comprises a plurality of measurement beams formed sequentially.

16. The device of claim 11, wherein said measurement beam comprises a plurality of measurement beams formed simultaneously.

17. The device of claim 11, wherein:
said measurement beam characteristic adjusted comprises an angle at which said measurement beam is aimed.

18. The device of claim 11, wherein the directed energy is selected from the group consisting of a radar beam and an ultrasonic beam.

19. The device of claim 11, wherein the measurement beam is formed using a phased array.

20. A product for measuring velocity of fluid flow in a channel, comprising:
a storage device having code stored therewith, the code being executable by a processor and comprising:
code that transmits, using a transmitter of a device, directed energy carrying a signal toward a surface of a fluid in a fluid channel, so as to produce one or more reflections from the fluid surface that substantially span the width of the fluid channel;
code that detects, by at least one receiver of the device, one or more received signals associated with the one or more reflections so produced; and
code that determines, based upon a measurement beam comprising characteristics of the transmitted and received signals, a fluid parameter to be measured using a processor of the device, wherein the determining comprises identifying, for each of the one or more received signals, a fluid parameter corresponding to the location of the corresponding received signal and determining a mean fluid parameter from the fluid parameters for each of the one or more received signals;
wherein, at least one measurement beam characteristic is adjusted based on a distance from the device to the fluid surface, wherein one of the at least one measurement characteristic that is adjusted comprises a width of the measurement beam and wherein adjustment of the width of the measurement beam comprises maintaining a width of the measurement beam contacting the surface of the fluid by widening the measurement beam as the distance from the device to the fluid surface is lessened.

* * * * *